(12) United States Patent
Umematsu et al.

(10) Patent No.: US 11,986,301 B2
(45) Date of Patent: May 21, 2024

(54) INFORMATION PROCESSING DEVICE, CONTROL METHOD, AND STORAGE MEDIUM

(71) Applicant: NEC Corporation, Tokyo (JP)

(72) Inventors: Terumi Umematsu, Tokyo (JP); Masanori Tsujikawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/009,850

(22) PCT Filed: Jun. 18, 2020

(86) PCT No.: PCT/JP2020/023979
§ 371 (c)(1),
(2) Date: Dec. 12, 2022

(87) PCT Pub. No.: WO2021/255899
PCT Pub. Date: Dec. 23, 2021

(65) Prior Publication Data
US 2023/0148924 A1    May 18, 2023

(51) Int. Cl.
*A61B 5/16*    (2006.01)
*A61B 5/00*    (2006.01)

(52) U.S. Cl.
CPC .......... *A61B 5/165* (2013.01); *A61B 5/0077* (2013.01); *A61B 5/7267* (2013.01); *A61B 5/7278* (2013.01); *A61B 2560/0242* (2013.01)

(58) Field of Classification Search
CPC ...... A61B 5/7278; A61B 5/7267; A61B 5/165
See application file for complete search history.

(56) References Cited

U.S. PATENT DOCUMENTS

| | | | |
|---|---|---|---|
| 2018/0202678 A1 | 7/2018 | Ahuja et al. | |
| 2020/0333033 A1 | 10/2020 | Kitagawa et al. | |
| 2021/0140660 A1 | 5/2021 | Kogo | |

FOREIGN PATENT DOCUMENTS

| | | |
|---|---|---|
| CN | 110378605 A | 10/2019 |
| JP | 2011-186521 A | 9/2011 |
| JP | 2015-017753 A | 1/2015 |
| JP | 2016-057057 A | 4/2016 |
| JP | 2017-205531 A | 11/2017 |
| JP | 2018-062190 A | 4/2018 |
| JP | 2019-096116 A | 6/2019 |
| WO | 2018/211559 A1 | 11/2018 |
| WO | 2019/087537 A1 | 5/2019 |

OTHER PUBLICATIONS

International Search Report for PCT Application No. PCT/JP2020/023979, dated Aug. 25, 2020.

*Primary Examiner* — Kesha Frisby
(74) *Attorney, Agent, or Firm* — Sughrue Mion, PLLC

(57) ABSTRACT

An information processing device 1X mainly includes an environmental information acquisition means 15X and a mental state estimation means 16X. The environmental information acquisition means 15X is configured to acquire environmental information "Ie" which is information on environment. The mental state estimation means 16X is configured to estimate, based on the environmental information Ie, a mental state of a group present in the environment indicated by the environmental information Ie.

10 Claims, 13 Drawing Sheets

100: MENTAL STATE ESTIMATION SYSTEM

INFORMATION PROCESSING DEVICE, CONTROL METHOD, AND STORAGE MEDIUM

This application is a National Stage Entry of PCT/JP2020/023979 filed on Jun. 18, 2020, the contents of all of which are incorporated herein by reference, in their entirety.

TECHNICAL FIELD

The present disclosure relates to the technical field of an information processing device, a control method and storage medium configured to estimate the mental state of a person.

BACKGROUND ART

There is a device or system configured to estimate the mental state of a person. For example, Patent Literature 1 discloses a system configured to estimate a stress level of a subject using biological information and environmental information regarding the subject.

CITATION LIST

Patent Literature

Patent Literature 1: JP 2019-096116A

SUMMARY

Problem to be Solved

It is conceivable to utilize the estimation results of the mental state when working toward a better environment, for example, to achieve productivity improvement and accident prevention. In this case, it is sometimes unrealistic to mount one or more sensors on each subject to estimate the mental state of the each subject.

In view of the above-described issue, it is therefore an example object of the present disclosure to provide an information processing device, a control method, and a storage medium capable of suitably estimating a mental state.

Means for Solving the Problem

In one mode of the information processing device, there is provided an information processing device including: an environmental information acquisition means configured to acquire environmental information which is information on environment; and a mental state estimation means configured to estimate, based on the environmental information, a mental state of a group present in the environment indicated by the environmental information.

In one mode of the control method, there is provided a control method executed by an information processing device, the control method including: acquiring environmental information which is information on environment; and estimating, based on the environmental information, a mental state of a group present in the environment indicated by the environmental information.

In one mode of the storage medium, there is provided a storage medium storing a program executed by a computer, the program causing the computer to function as: an environmental information acquisition means configured to acquire environmental information which is information on environment; and a mental state estimation means configured to estimate, based on the environmental information, a mental state of a group present in the environment indicated by the environmental information.

Effect

An example advantage according to the present invention is to suitably estimate the mental state of a group present in an environment of interest.

EXAMPLE EMBODIMENTS

Hereinafter, an example embodiment of an information processing device, a control method, and a storage medium will be described with reference to the drawings.

First Example Embodiment (1) System Configuration

Figure 1:
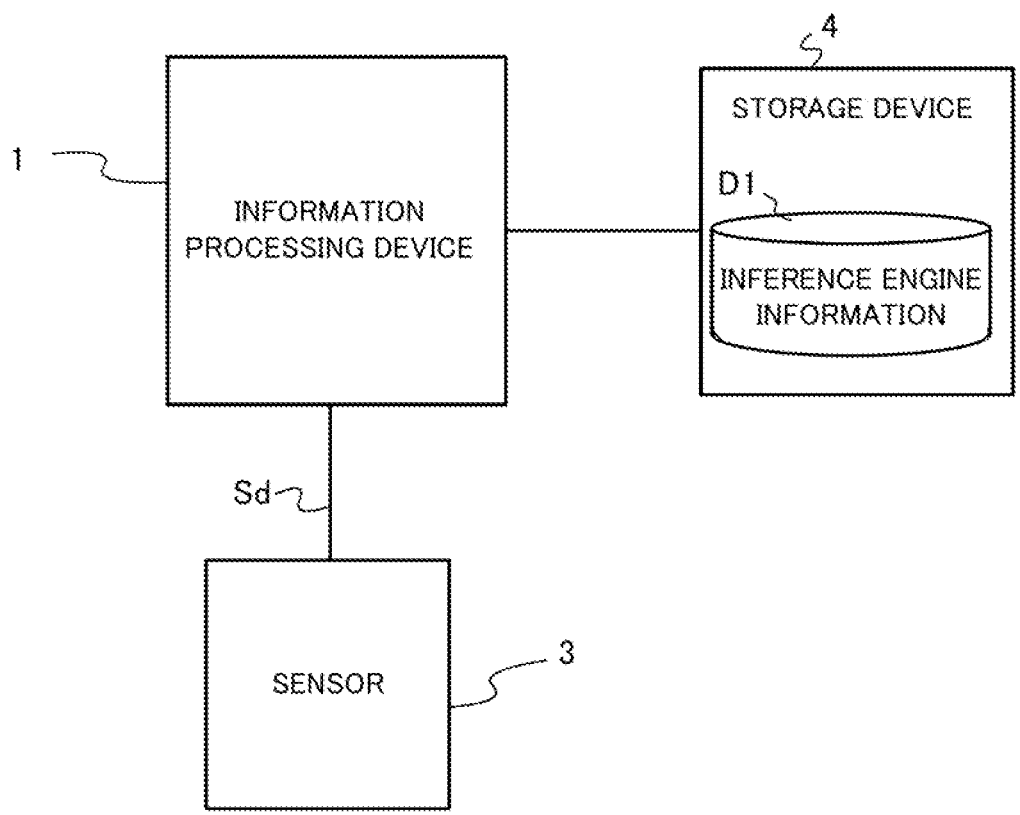
FIG. 1 illustrates a configuration of a mental state estimation system according to a first example embodiment.

FIG. 1 shows the configuration of the mental state estimation system 100 according to the first example embodiment. The mental state estimation system 100 mainly includes an information processing device 1, a sensor 3, and a storage device 4.

The mental state estimation system 100 suitably estimates the mental state of a group (population) present in a space (referred to as "target space Stag") of interest based on information on an environment in the target space Stag. The term "group" described above refers to, in other words, all person(s) present in the target space Stag and the number of the person(s) may be one or may be more than one. Further, the target space Stag may be either indoors or outdoors. Examples of the target space Stag include a space in which one or more outdoor facilities (such as a park, an outdoor concert venue, and a station square) exist, a space in an indoor facility (such as a store, event hall, and a building or a part thereof), a space in a vehicle such as a train and a bus, and an area identified according to administrative districts.

The information processing device 1 performs data communication with the sensor 3 and the storage device 4 through a communication network or directly by wired or wireless communication. Then, the information processing device 1 estimates the mental state of the target group based on a sensor signal "Sd" supplied from the sensor 3 and the information stored in the storage device 4. Thereafter, the information processing device 1 may further perform a predetermined control based on the estimation result of the mental state. As examples of the above-described control, the information processing device 1 may perform display control for presenting the estimation result of the mental state to the user, or may perform operation control of a device for changing the mental state of the group to a desired mental state. Such control may be performed by an external device configured to receive the estimation result of the mental state from the information processing device 1.

The sensor 3 is one or more sensors for detecting (sensing) information necessary for generating information (also referred to as "environmental information Ie") relating to the environment in the target space Stag, and supplies a sensor signal "Sd" indicating the detection result to the information processing device 1. Here, examples of the environmental information Ie include information indicating the degree of the environmental inferiority (poorness) in the target space Stag and information directly or indirectly indicating the degree of the congestion of the group in the target space Stag or indicating the number of people belonging to the group in the target space Stag. The sensor 3 detects information to be used for generating such environmental information Ie.

Here, the sensor signal Sd to be used for generating the environmental information Ie relating to the degree of the environmental inferiority is a signal outputted by a measuring instrument which measures any gaseous information such as temperature, humidity, carbon dioxide concentration, oxygen concentration, and carbon monoxide concentration. In another example, the sensor signal Sd to be used for generating the environmental information Ie indicating the degree of the environmental inferiority is a signal outputted by an illuminance sensor for measuring the illuminance. Further, the sensor signal Sd to be used for generating the environmental information Ie relating to the degree of the congestion of the group in the target space Stag or indicating the number of people belonging to the group may be a signal outputted by a camera (photographing unit) for generating an image obtained by photographing the target space Stag. In this case, the information processing device 1 can grasp the number of detected people using a measure for automatically detecting people through an image generated by the camera, and thereby estimate the number of the people belonging to the group in the target space Stag or the degree of the congestion of the group in the target space Stag. In another example, the sensor signal Sd to be used for generating the environmental information Ie relating to the degree of the congestion of the group in the target space Stag or indicating the number of people of the group may be a signal outputted by a human detecting sensor provided in the target space Stag. In still another example, the sensor signal Sd to be used for generating the environmental information Ie relating to the degree of the congestion of the group in the target space Stag or indicating the number of people belonging to the group may be a signal outputted by an IC (Integrated Circuit) card reader or the like for entry and exit management by use of an IC card such as an employee card. In still another example, the sensor signal Sd to be used for generating the environmental information Ie relating to the degree of the congestion of the group in the target space Stag or indicating the number of people belonging to the group may be a signal outputted by a sensor configured to measure the weight of a vehicle such as a train, bus, or the like. In still other examples, the sensor signal Sd to be used for generating the environmental information Ie relating to the degree of the congestion of the group in the target space Stag or indicating the number of people of the group may be a signal outputted by a device configured to measure the amount (e.g., bandwidth) of the communication network such as a wireless LAN (Local Area Network) or GPS (Global Positioning System). Examples of the above-mentioned device include radio LAN equipment and a GPS receiver.

The storage device 4 is one or more memories configured to store various kinds of information necessary for estimating the mental state of the group by the information processing device 1. The storage device 4 may be an external storage device such as a hard disk connected to or built in to the information processing device 1, or may be a storage medium such as a flash memory. The storage device 4 may be a server device that performs data communication with the information processing device 1. The storage device 4 may be configured by a plurality of devices. The storage device 4 stores the inference machine information D1.

The inference engine information D1 indicates parameters required to configure the inference engine which performs an inference on the mental state of the target group based on the environmental information Ie. The inference engine may be a model based on a machine learning, such as a neural network or a support vector machine, or may be a statistical model, such as a regression model. For example, if the model of the inference engine described above is a neural network such as a convolutional neural network, the inference engine information D1 includes various parameters regarding the layer structure, the neuron structure of each layer, number of filters and filter sizes in each layer, and weights of each element of each filter. Further, when the information processing device 1 performs an inference on a plurality of indices representing the mental state, the inference engine information D1 may include parameters of the inference engine provided for each index representing the mental state.

The configuration of the mental state estimation system 100 shown in FIG. 1 is an example, and various changes may be made to the configuration. For example, the information processing device 1 may incorporate, or may be electrically connected to, at least one of an input device for receiving an input from a user and an output device (e.g., a display, a speaker, or the like) for outputting predetermined information to the user. Further, the information processing device 1 may be configured by a plurality of devices. In this case, the plurality of devices functioning as the information processing device 1 perform the transmission and reception of information necessary for executing the pre-allocated processing among the plurality of devices.

(2) Hardware Configuration

Figure 2:
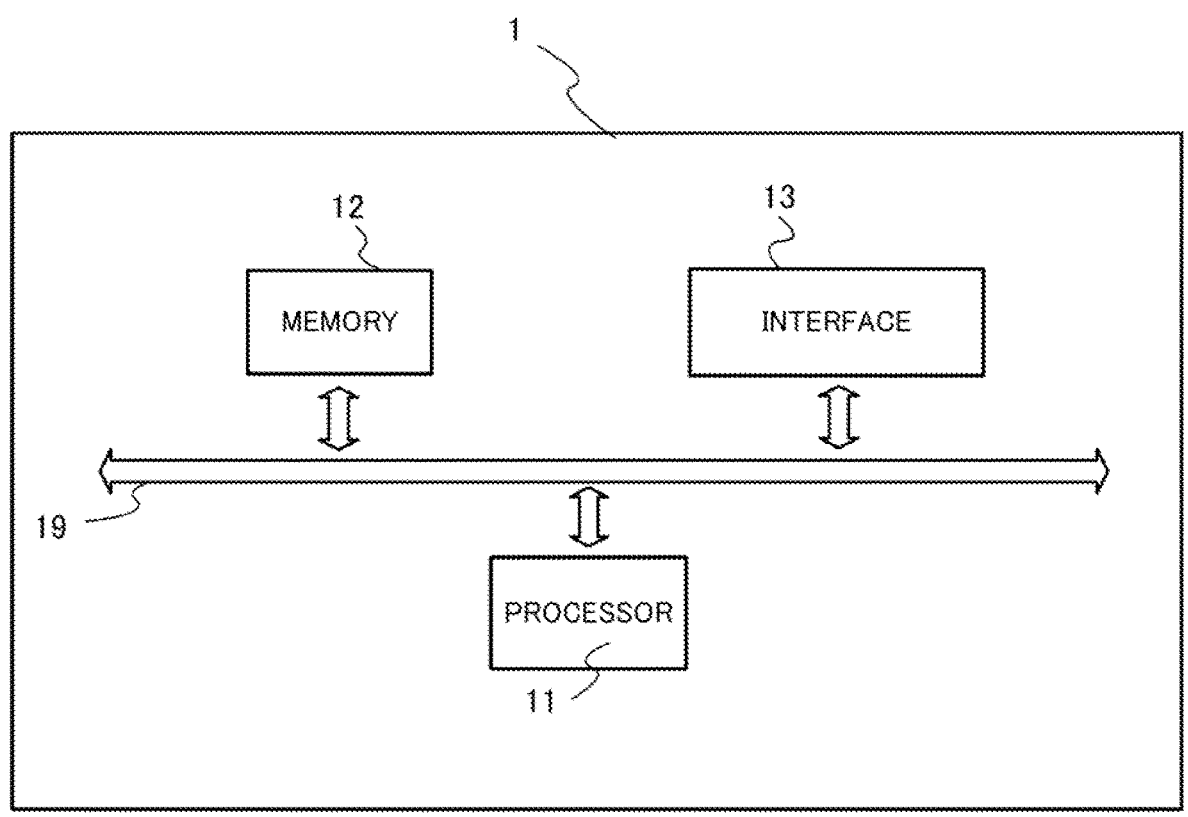
FIG. 2 illustrates a hardware configuration of an information processing device.

FIG. 2 shows the hardware configuration of the information processing device 1. The information processing device 1 includes a processor 11, a memory 12, and an interface 13 as hardware. The processor 11, the memory 12, and the interface 13 are connected via a data bus 19 to one another.

The processor 11 executes a predetermined process by executing a program stored in the memory 12. The processor 11 is one or more processors such as a CPU (Central Processing Unit), GPU (Graphics Processing Unit), and a quantum processor.

The memory 12 is configured by various volatile and non-volatile memories such as RAM (Random Access Memory), ROM (Read Only Memory), and the like. A program executed by the information processing device 1 is stored in the memory 12. The memory 12 is used as a working memory and temporarily stores information acquired from the storage device 4. The memory 12 may function as a storage device 4. The storage device 4 may function as a memory 12 of the information processing device 1. The program to be executed by the information processing device 1 may be stored in a storage medium other than the memory 12.

The interface 13 is one or more interfaces for electrically connecting the information processing device 1 to other devices. For example, one of the interfaces for connecting the information processing device 1 to other devices may be a communication interface such as a network adapter for performing transmission and reception of data to and from other devices through wired or wireless communication under the control of the processor 11. In other examples, the information processing device 1 may be connected to other devices by a cable or the like. In this instance, the interface 13 includes a hardware interface compliant with USB (Universal Serial Bus), SATA (Serial AT Attachment), or the like for exchanging data with other devices. The interface 13 may also perform interface operation with various external devices such as an input device, a display device, a sound output device, and the like.

The hardware configuration of the information processing device 1 is not limited to the configuration shown in FIG. 2. For example, the information processing device 1 may include at least one of an input unit, a display unit, or a sound output unit.

(3) Functional Block

Figure 3:
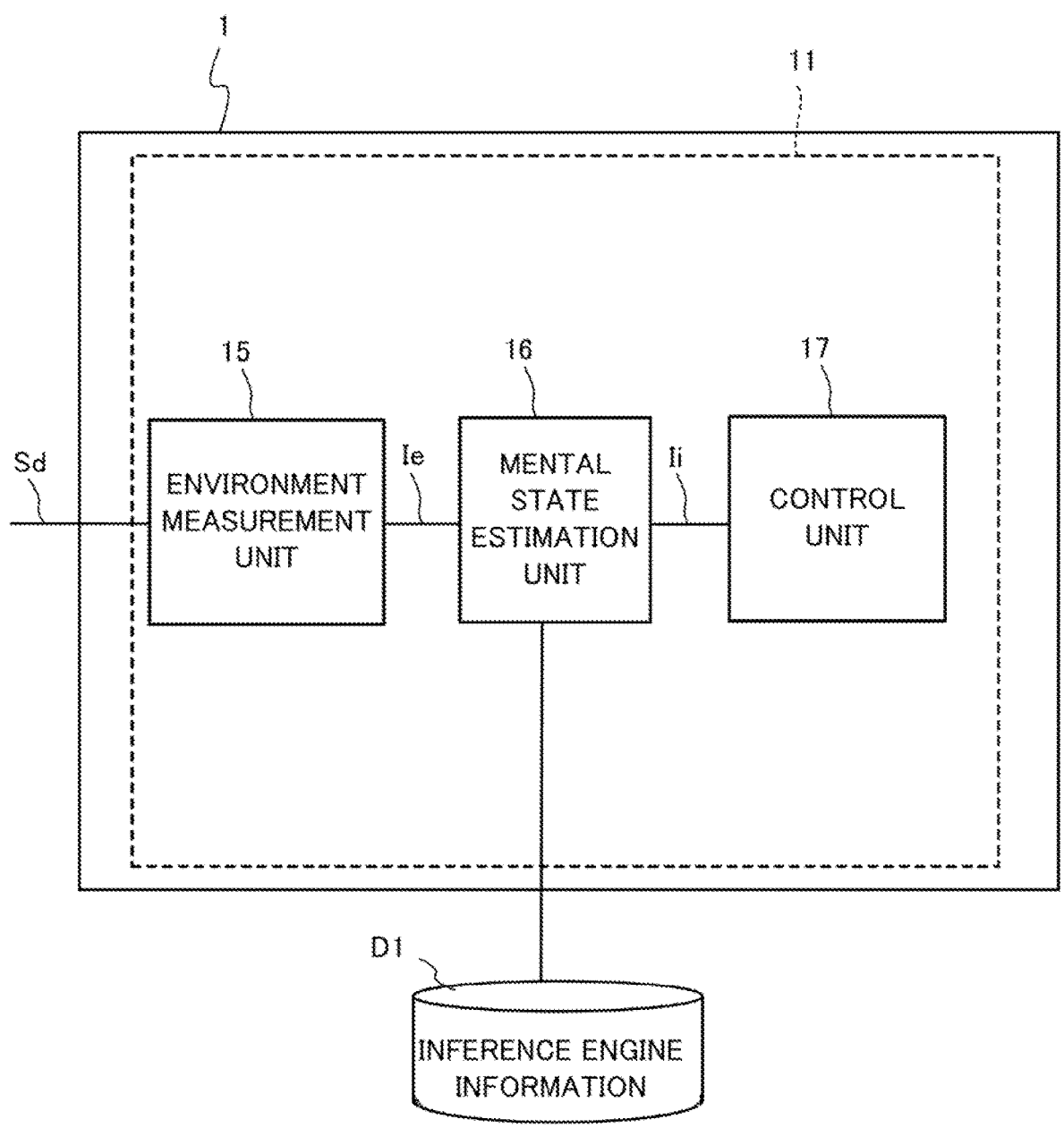
FIG. 3 illustrates an example of a functional block of the information processing device.

FIG. 3 illustrates an example of the functional block of the information processing device 1 relating to the estimation process of the mental state of the group in the target space Stag. The processor 11 of the information processing device 1 functionally includes an environment measurement unit 15, a mental state estimation unit 16, and a control unit 17. In FIG. 3, the blocks to exchange data with each other are connected to each other by a solid line. However, the combinations of the blocks to exchange data are not limited to the combinations shown in FIG. 3. The same applies to other functional block diagrams to be described later.

The environment measurement unit 15 measures the environment of the target space Stag based on the sensor signal Sd supplied from the sensor 3, and generates an environmental information Ie corresponding to the measurement result. For example, the environment measurement unit 15 generates, based on the sensor signal Sd, the environmental information Ie directly or indirectly indicating at least one of: the degree of the environmental inferiority in the target space Stag; the number of people belonging to the group in the target space Stag; or the degree (e.g., the number of people per unit area) of the congestion of the people belonging to the group in the target space Stag. In this case, for example, the environment measurement unit 15 calculates the environmental information Ie from the sensor signal Sd, by referring to a look-up table or parameters for configuring a calculator (including a calculation formula) which are stored in advance in the memory 12. The calculator may be, for example, any learning model that is learned to calculate the environmental information Ie when an image of the target space Stag or another sensor signal Sd is inputted thereto. The environment measurement unit 15 supplies the generated environmental information Ie to the mental state estimation unit 16.

The mental state estimation unit 16 performs estimation on the mental state of the group in the target space Stag based on the environmental information Ie supplied from the environment measurement unit 15. Then, the mental state estimation unit 16 supplies information (also referred to as "mental state information Ii") indicating the estimated mental state to the control unit 17. In this case, the mental state estimation unit 16 configures the inference engine by referring to the inference engine information D1, and acquires the mental state information Ii by inputting the environmental information Ie to the configured inference engine. Here, the mental state estimation unit 16 generates the mental state information Ii indicating index values regarding at least one of: the degree of the stress of the group present in the target space Stag; the degree of the comfort thereof; the degree of the (mental) health thereof; the degree of the happiness thereof; or any other index of the mental state thereof. Details of the processing executed by the mental state estimation unit 16 will be described later.

The control unit 17 performs a predetermined control based on the mental state information Ii supplied from the mental state estimation unit 16. As a first example, the control unit 17 performs the control to store the mental state information Ii in the memory 12 or the storage device 4 in association with the estimation date and time and the identification information of the target space Stag. As a second example, the control unit 17 controls an output device (not shown) to output the mental state information Ii. In this case, the control unit 17 performs, based on the mental state information Ii, an evaluation (e.g., evaluation regarding whether or not the mental state is within an allowable range) on the quality of the mental state of the target group, and outputs information (e.g., displays or outputs by audio the necessity of temperature adjustment) in accordance with the evaluation result. As a third example, based on the mental state information Ii, the control unit 17 controls one or more devices for adjusting the environment in the target space Stag. In this case, the control unit 17 may perform the same evaluation as the second example to perform control of the devices in accordance with the evaluation result. As a fourth example, the control unit 17 may transmit the mental state information Ii to an external device configured to perform the output control according to the second example or perform the device control based on the third example according to the second example.

Each component of the environment measurement unit 15, the mental state estimation unit 16, and the control unit 17 described in FIG. 3 can be realized, for example, by the processor 11 executing the program stored in the memory 12 or the storage device 4. In addition, the necessary programs may be recorded in any nonvolatile recording medium and installed as necessary to realize each component. Each of these components is not limited to being implemented by software using a program, and may be implemented by any combination of hardware, firmware, and software. Each of these components may also be implemented using user programmable integrated circuitry, such as, for example, FPGA (Field-Programmable Gate Array) or a microcomputer. In this case, the integrated circuit may be used to realize a program functioning as each of the above-described components. Thus, each component may be implemented in hardware other than a processor. The above is the same in other example embodiments to be described later.

(4) Details of Mental State Estimation Unit

Next, a description will be given of the details of the processing executed by the mental state estimation unit 16.

Figure 4A:
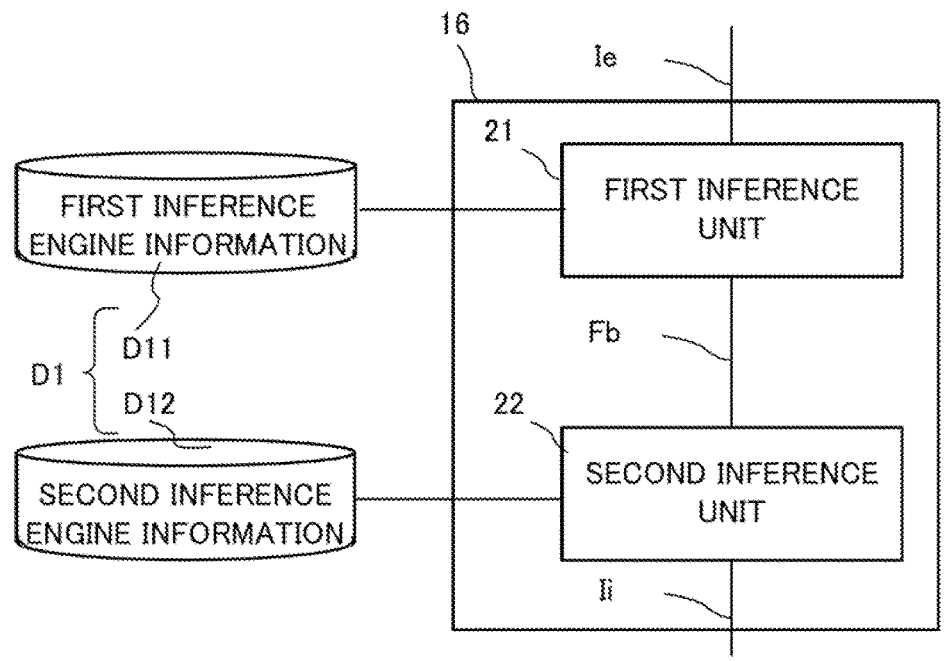
FIG. 4A illustrates a first example of a functional block of a mental state estimation unit.

FIG. 4A shows a first example of the functional block of the mental state estimation unit 16. In the first example, the mental state estimation unit 16 includes a first inference unit 21, and a second inference unit 22. The inference engine information D1 also includes first inference engine information D11 and second inference engine information D12.

The first inference unit 21 performs, based on the environmental information Ie, an inference on features (feature values) regarding the estimated biological information (also referred to as "biological information feature values Fb") of the target group. In this case, the first inference unit 21 refers to the first inference engine information D11 and configures an inference engine (also referred to as "first inference engine") which is learned to infer the biological information feature values Fb when the environmental information Ie is inputted thereto. Then, the first inference unit 21 receives the environmental information Ie to the configured first inference engine to acquire the biological information feature values Fb. Here, the first inference engine may be a model based on machine learning, such as a neural network and a support vector machine, or may be a statistical model, such as a regression model. Examples of the biological information include information on heart rate, amount of perspiration, skin temperature, or amount of movement. The first inference unit 21 may calculate the biological information feature values Fb which correspond to the feature values of a single type of the biological information, or may calculate plural sets of biological information feature values Fb which correspond to the feature values of plural types of the biological information. In the latter case, for example, the first inference engines may be provided according to the number of the plural sets of the biological information feature values Fb, and the inference engine information D1 may include the parameters of the first inference engines configured to calculate the plural sets of the biological information feature values Fb. In another example, the first inference engine may be learned to infer the plural sets of the biological information feature values Fb from the environmental information Ie.

The second inference unit 22 outputs the mental state information Ii indicating one or more index values of the mental state on the basis of the biological information feature values Fb. In this case, the second inference unit 22 refers to the second inference engine information D12 and configures an inference engine (also referred to as "second inference engine") which is learned to output mental state information Ii indicating one or more index values of the mental state when the biological information feature values Fb are inputted thereto. Then, the second inference unit 22 outputs the mental state information Ii indicating the index values of the mental state by inputting the biological information feature values Fb to the configured second inference engine.

Here, the second inference engine may be a model based on machine learning or may be a statistical model such as a regression model. Further, the second inference engine may be a threshold value, a simple formula, or a look-up table for determining one or more index values of the mental state from the biological information feature values Fb. Further, the second inference engine information D12 for configuring the second inference engine may be information prepared in advance based on various established methods or findings (knowledge base) for estimating the mental state of a person from biological information or feature values of the person.

The second inference unit 22 may output mental state information Ii indicating an index value of a single mental state or may output mental state information Ii indicating plural index values of the mental state. In the latter case, for example, a second inference engine is provided for each index of the mental state to be calculated, and the second inference unit 22 generates the mental state information Ii using an appropriate second inference engine for the each index of the mental state to be calculated. In this case, the parameters of the second inference engine associated with the each index of the mental state are included in the second inference engine information D12. In another example, the second inference unit 22 may output mental state information Ii indicating plural index values of the mental state using a single second inference engine. In this case, for example, the second inference unit 22 receives, from the first inference unit 21, plural sets of the biological information feature values Fb, and sets the weight for each set of the biological information feature values Fb to be inputted to the second inference engine for the each index of the mental state to be calculated. In this case, for example, the second inference engine information D12 includes information on the weight value to be applied to the each set of the biological information feature values Fb for the each index of the mental state to be calculated. The second inference engine may be learned to output the mental state information Ii indicating one or more index values of the mental state from plural sets of the biological information feature values Fb without using information on the weight value as described above.

Figure 4B:
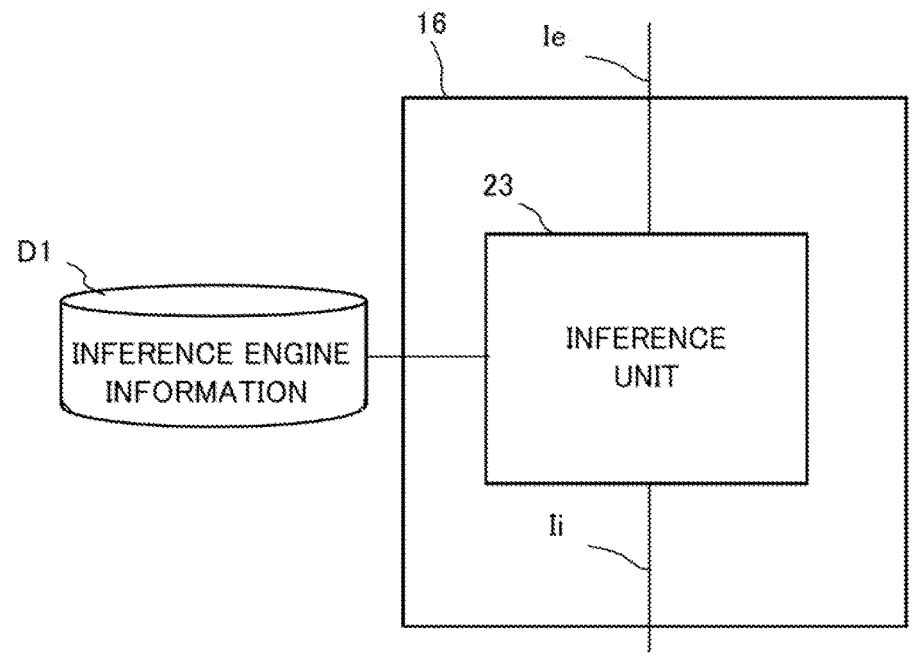
FIG. 4B illustrates a second example of a functional block of the mental state estimation unit.

FIG. 4B shows a second example of the functional block of the mental state estimation unit 16. In the second example, the mental state estimation unit 16 includes an inference unit 23. The inference unit 23 refers to the inference engine information D1 and configures an inference engine (also referred to as "third inference engine") that is learned to directly output the mental state information Ii from the environmental information Ie. Then, the inference unit 23 acquires the mental state information Ii by inputting the environmental information Ie to the third inference engine. Here, the third inference engine may be a model based on machine learning or may be a statistical model such as a regression model. In this case, the inference engine information D1 includes parameters and the like for configuring the third inference engine. When there are a plurality of indices of the mental state to be calculated, the inference engine information D1 may include parameters of the third inference engine for each of the indices of the mental state to be calculated.

Accordingly, by adopting any of the configurations according to the first example and the second example, the mental state estimation unit 16 can suitably generate the mental state information Ii indicating the mental state of the target group.

(5) Learning of Inference Engine

Figure 5:
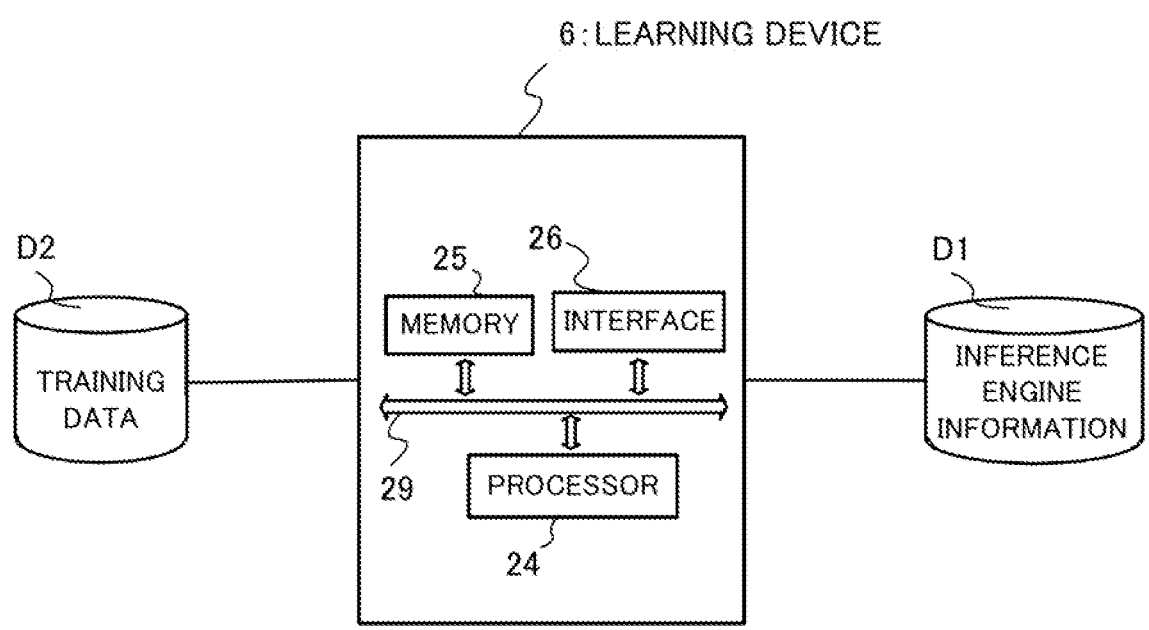
FIG. 5 is a schematic configuration diagram of a system configured to generate inference engine information.

Next, a description will be given of the generation of the inference engine information D1 to be executed prior to the estimation on the mental state of the group by the information processing device 1. FIG. 5 is a schematic configuration diagram of a system that generates inference engine information D1. The system includes a learning device 6 configured to refer to the training data D2.

For example, the learning device 6 has the same configuration as the configuration of the information processing device 1 illustrated in FIG. 2, and mainly includes a processor 24, a memory 25, an interface 26, and a data bus 29 that electrically connects these components. Then, the learning device 6 refers to the training data D2 and generates and updates the inference engine information D1 by performing at least one of the training of the first inference engine, the second inference engine, or the third inference engine described above. The learning device 6 may be an information processing device 1, or may be any device other than the information processing device 1.

The training data D2 is a training dataset that includes combinations of input data and correct answer data to train an inference engine. The training data D2 includes a training dataset to be used for training at least one of the first inference engine, the second inference engine, or the third inference engine described above.

Figure 6A:
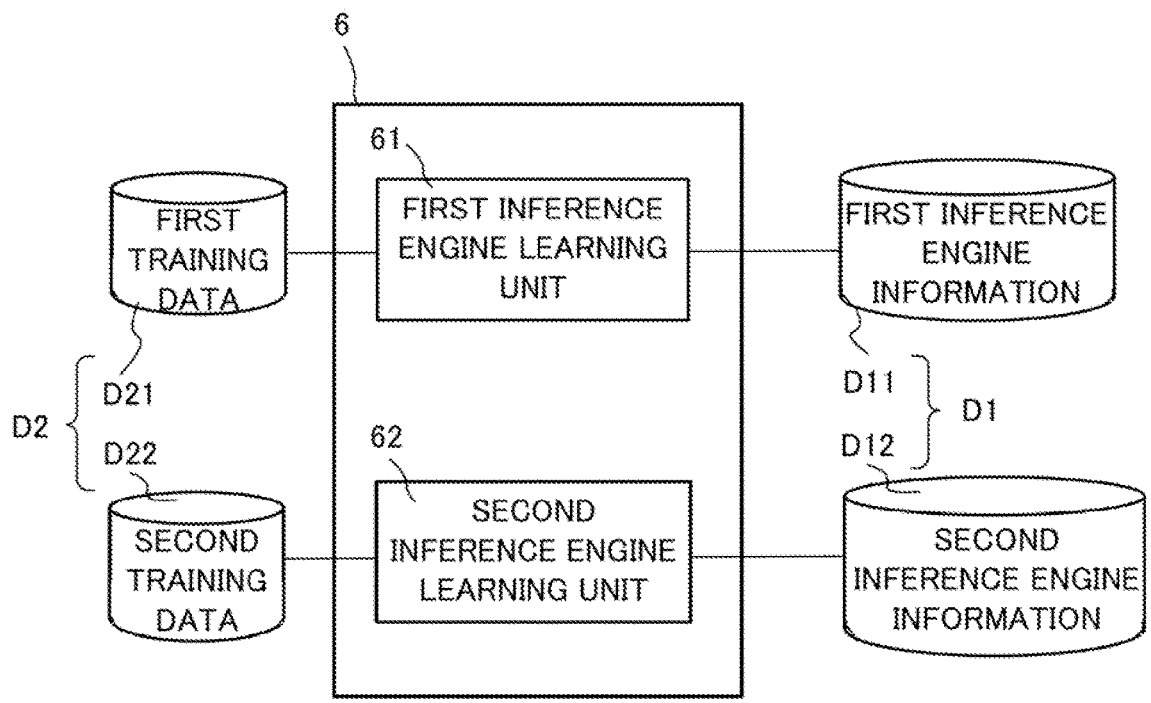
FIG. 6A illustrates a first example of a functional block of a learning device.

FIG. 6A shows a first example of a functional block of the learning device 6. In the first example, the learning device 6 performs the learning (training) of the first inference engine and the second inference engine to be used by the mental state estimation unit 16 shown in FIG. 4A, and includes the first inference engine learning unit 61 and the second inference engine learning unit 62. The first inference engine learning unit 61 and the second inference engine learning unit 62 are realized by, for example, the processor 24 of the learning device 6. The training data D2 includes first training data D21 and second training data D22. Here, the first training data D21 is a training dataset that includes a plurality of combinations of environmental information Ie and biological information feature values Fb. The second training data D22 is a training dataset that includes a plurality of combinations of biological information feature values Fb and mental state information Ii that indicates one or more index values of the mental state.

In this case, the first inference engine learning unit 61 performs the training of the first inference engine using the environmental information Ie included in the first training data D21 as the input data and using the bioinformation feature values Fb as the correct answer data. In this case, the first inference engine learning unit 61 determines the parameters of the first inference engine so that the error (loss) between the inference result outputted by the first inference engine when the environmental information Ie is inputted thereto and the biological feature values Fb which are the correct answer data is minimized. The algorithm for determining the parameters described above to minimize loss may be any learning algorithm used in machine learning, such as a gradient descent method and an error back-propagation method. Similarly, the second inference engine learning unit 62 performs the training of the second inference engine using the biological information features Fb included in the second training data D22 as the input data and using the mental state information Ii indicating one or more index values of the mental state as the correct answer data.

According to the first exemplary example embodiment, the learning device 6 can suitably generate the first inference engine information D11 and the second inference engine information D12 required to configure the first inference engine and the second inference engine to be used by the mental state estimation unit 16 shown in FIG. 4A.

Figure 6B:
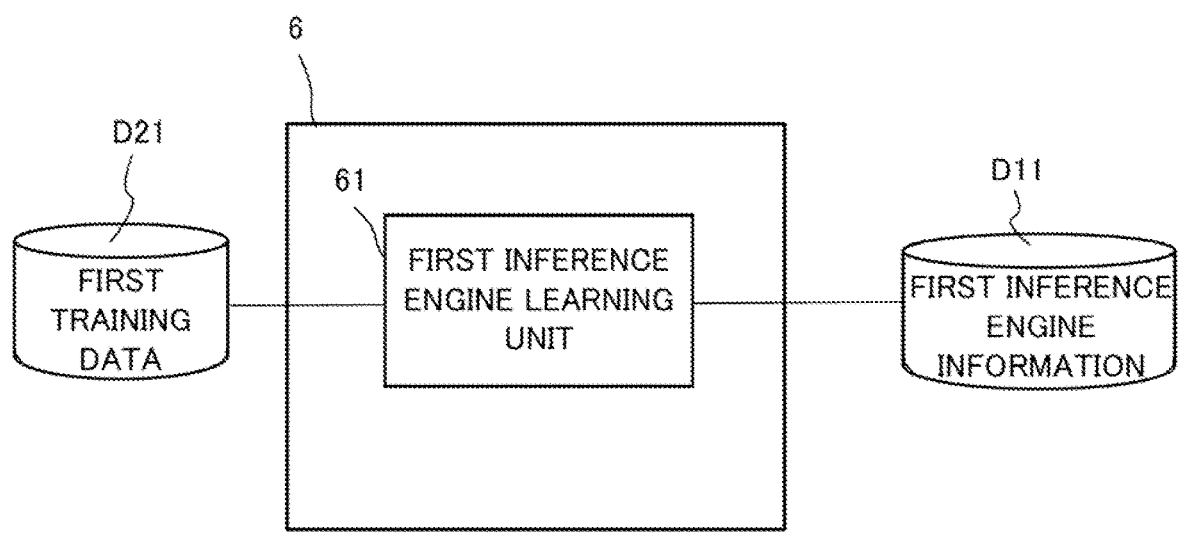
FIG. 6B illustrates a second example of a functional block of the learning device.

FIG. 6B shows a second example of a functional block of the learning device 6. In the second example, the learning device 6 performs the learning (training) of the first inference engine to be used by the mental state estimation unit 16 shown in FIG. 4A, and includes the first inference engine learning unit 61. In the second example, the parameters for configuring the second inference engine has already been obtained as the second inference engine information D12, and the learning device 6 performs only the learning of the first inference engine without performing the learning of the second inference engine. Even according to the second example, the learning device 6 can suitably generate the first inference engine information D11 to be used by the mental state estimation unit 16 shown in FIG. 4A.

Figure 7A:
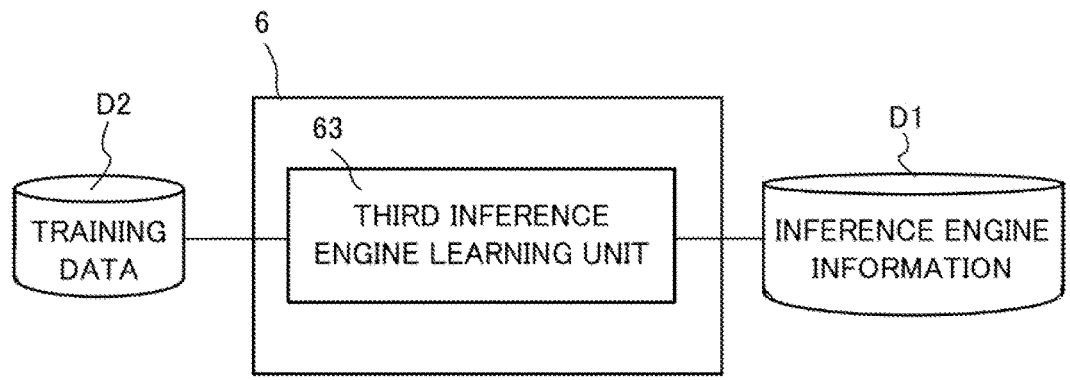
FIG. 7A illustrates a third example of a functional block of the learning device.

FIG. 7A shows a third example of a functional block of the learning device 6. In the third example, the learning device 6 performs the learning (training) of the third inference engine to be used by the mental state estimation unit 16 shown in FIG. 4B, and has the third inference engine learning unit 63. Further, in the third example, the training data D2 includes combinations of the environmental information Ie and the mental state information Ii which indicates one or more index values of the mental state as a training dataset. In this case, the above-mentioned term "index values of the mental state" includes index values of the mental state obtained not only from the detected biological information but also from a questionnaire. The third inference engine learning unit 63 performs the learning of the third inference engine using the environmental information Ie included in the training data D2 as the input data and using the mental state information Ii indicating one or more index values of the mental state as the correct answer data. Accordingly, the learning device 6 can suitably generate the inference engine information D1 required to configure the third inference engine to be used by the mental state estimation unit 16 shown in FIG. 4B.

Figure 7B:
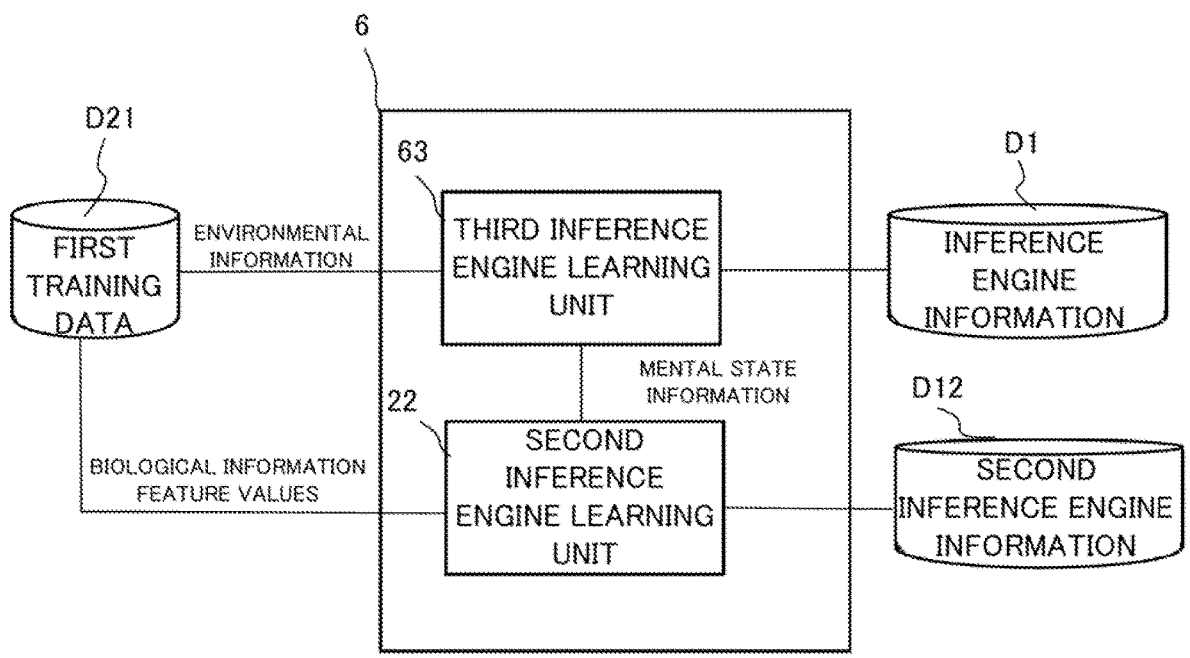
FIG. 7B illustrates a fourth example of a functional block of the learning device.

FIG. 7B shows a fourth example of a functional block of the learning device 6. In the fourth example, the learning device 6 performs the learning of the third inference engine to be used by the mental state estimation unit 16 shown in FIG. 4B, and includes the second inference unit 22 and the third inference engine learning unit 63. Further, the learning device 6 refers to the first training data D21 including a plurality of combinations of the environmental information Ie and the biological information feature values Fb as a training dataset.

The second inference unit 22 configures a second inference engine by referring to the second inference unit information D12. Then, the second inference unit 22 extracts a set of biological information feature values Fb registered as correct answer data in the first training data D21, and generates a mental state information Ii indicating one or more index values of the mental state from the set of the biological information feature values Fb using the second inference engine. Then, the second inference unit 22 supplies the mental state information Ii indicating the inferred index values of the mental state to the third inference engine learning unit 63 as the correct answer data.

The third inference engine learning unit 63 acquires, from the first training data D21 as the input data, the environmental information Ie corresponding to the biological information feature values Fb which is supplied to the second inference unit 22, and acquires the mental state information Ii outputted by the second inference unit 22 as the correct answer data. Then, the third inference engine learning unit 63 performs the training of the third inference engine based on the combinations of the acquired environmental information Ie and the mental state information Ii. Then, the third inference engine learning unit 63 generates parameters of the third inference engine obtained through the training as the inference engine information D1.

Here, a supplementary description will be given of the effect of the fourth example. In order to obtain the mental state information Ii indicating one or more index values of the mental state that are correct answer data in the third example, it is necessary to carry out a survey for people in the environment indicated by the environmental information Ie serving as the input data, which generally requires a lot of labor. Considering the above, in the fourth example, the learning device 6 uses the first training data D21 that does not require the index values of the mental state, and generates the mental state information Ii that is the correct answer data of the third inference engine based on the second inference engine prepared in advance. Thus, the learning device 6 can suitably generate the inference engine information D1 required for the configuration of the third inference engine for outputting the mental state information Ii from the environmental information Ie.

(6) Processing Flow

Figure 8:
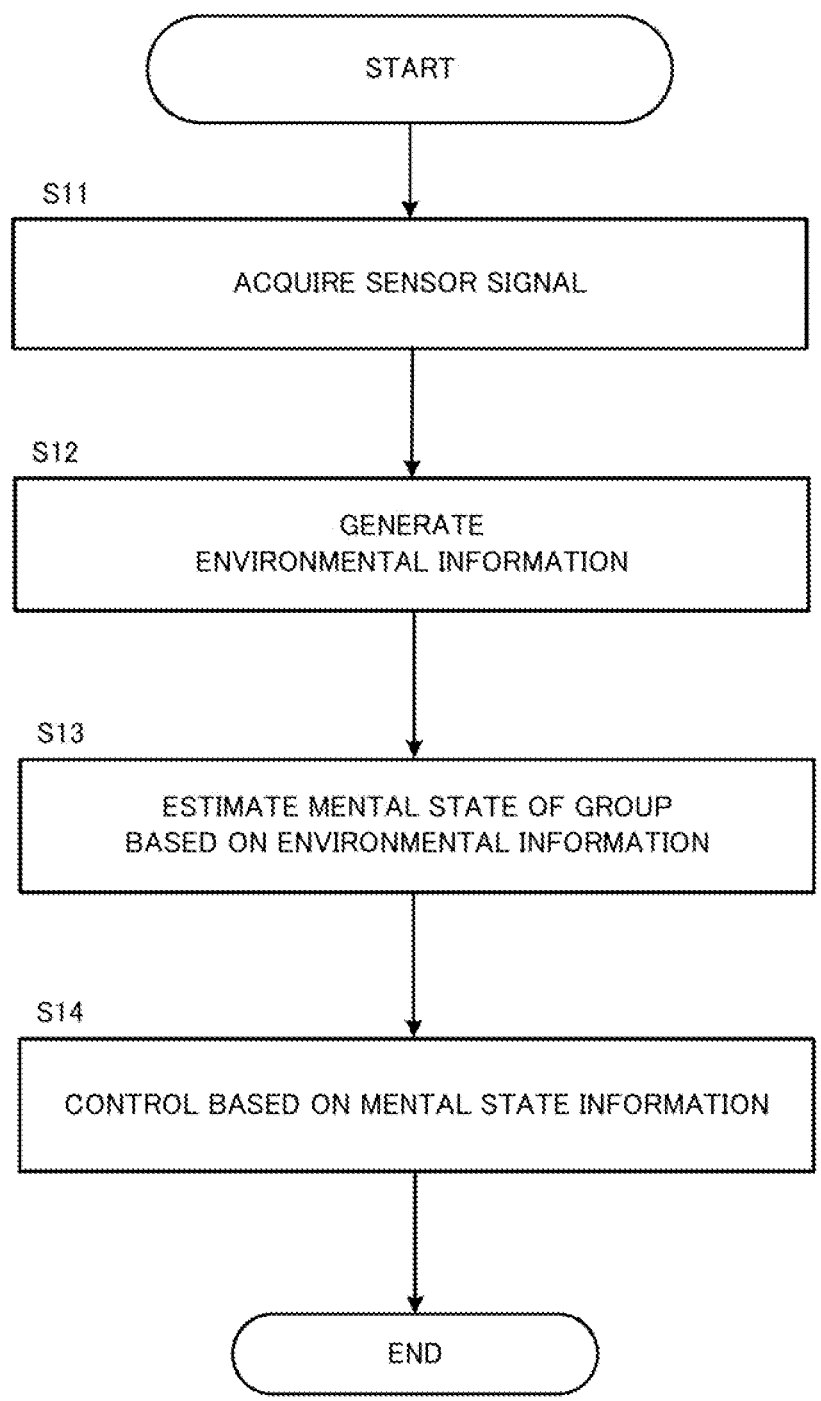
FIG. 8 is an example of a flowchart showing a procedure of the process performed by the information processing device in the first example embodiment.

FIG. 8 is an example of a flowchart showing a processing procedure executed by the information processing device 1 in the first example embodiment. The information processing device 1 may perform the processing of the flowchart shown in FIG. 8 at a timing specified by the user or may perform the processing at predetermined time intervals.

First, the information processing device 1 acquires the sensor signal Sd generated by the sensor 3 (step S11). In this case, the information processing device 1 receives the sensor signal Sd relating to the environment in the target space Stag from the sensor 3 via the interface 13. Then, the environment measurement unit 15 of the information processing device 1 generates environmental information Ie based on the sensor signal Sd acquired at step S11 (step S12). In this case, for example, as the environmental information Ie, the environment measurement unit 15 generates information indicating directly or indirectly at least one of: the degree of the environmental inferiority in the target space Stag; the number of people in the target space Stag; or the degree of congestion in the target space Stag.

Next, the mental state estimation unit 16 of the information processing device 1 performs estimation on the mental state of the group in the target space Stag on the basis of the environmental information Ie generated at step S12 (step S13). In this case, the mental state estimation unit 16 configures an inference engine by referring to the inference engine information D1 and inputs the environmental information Ie to the configured inference engine, thereby to acquire the mental state information Ii. In this case, the above-mentioned inference engine may be a combination of the first inference engine and the second inference engine (see FIG. 4A), or may be a third inference engine (see FIG. 4B). Then, the control unit 17 performs the control based on the mental state information Ii generated by the mental state estimation unit 16 (step S14).

(7) Modifications

Instead of performing the estimation on the mental state of the group at the present time by processing the sensor signal Sd generated by the sensor 3 in real time, the information processing device 1 may perform the estimation on the mental state of the group at any previous time based on the information that is accumulated sensor signals Sd generated by the sensor 3.

Figure 9:
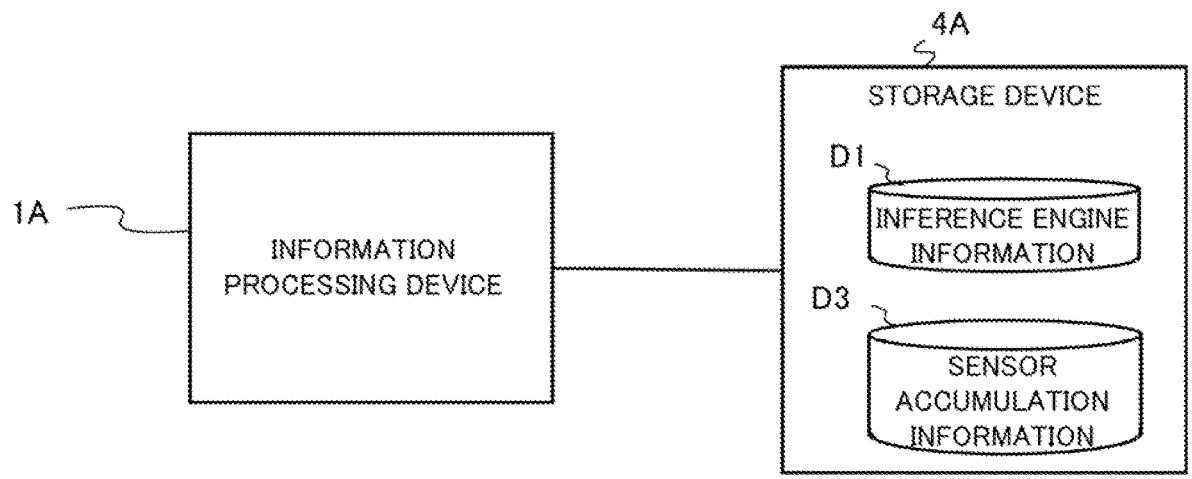
FIG. 9 illustrates a schematic configuration of the mental state estimation system according to a modification.

FIG. 9 shows a schematic configuration of a mental state estimation system 100A according to a modification. In this modification, the storage device 4A stores the sensor storage information D3. Here, the sensor accumulation information D3 is the accumulated sensor signals Sd generated by the sensor 3 shown in FIG. 1, and the date and time information (time stamp) or the like generated by the sensor 3 is associated with each sensor signal Sd. The information processing device 1A has the same configuration as the configuration of the information processing device 1 shown in FIGS. 2 and 3 and the like. Then, for example, the information processing device 1A extracts the sensor signal(s) Sd corresponding to the time or time slot specified by the user input or the like from the sensor accumulation information D3, and estimates the mental state of the group in the target space Stag corresponding to the specified time or time slot.

Thus, the information processing device 1A according to the modification can perform the estimation on the mental state of the group at any timing in the past by referring to the sensor accumulation information D3 that is accumulated sensor signals Sd generated in the past.

(8) Effect

Next, a supplementary description will be given of the effect according to the first example embodiment.

There are situations in which estimation on the general mental state of a group becomes important when working toward a better environment, for example, to achieve productivity improvement and accident prevention. In order to measure the mental state of a person, it is common to have the person wear a sensor which acquires its biological information, but it is not realistic to have everyone under that environment wear sensors. In view of the above, the information processing device 1 or the information processing device 1A according to the present example embodiment estimates the mental state of the group with high accuracy using the environmental information that can be obtained easier than the biological information.

Besides, the estimation result of the mental state of the group estimated by information processing device 1 or information processing device 1A can be widely utilized in various fields such as urban transportation, urban planning, public health, and change of in-store environment. For example, according to the estimation result of the past mental state of the passengers in a vehicle such as a train, it is possible to reexamine the time table so that the mental state of the passengers becomes a desirable state. In other examples, the vehicle departure time can also be changed or adjustment of air conditioning in the vehicle can be made according to the estimation result of the mental state of the passengers in real time in the vehicle. It is also possible to detect a location where the mental state of a group is always favorable, thereby to select the detected location as a candidate for tourist spots. It is also conceivable to change the flow line, change the arrangement of goods, or restrict the entrance so that the mental state of customers in a store becomes a desirable state according to the estimation result of the mental state of the customers in the store.

Second Example Embodiment

Figure 10:
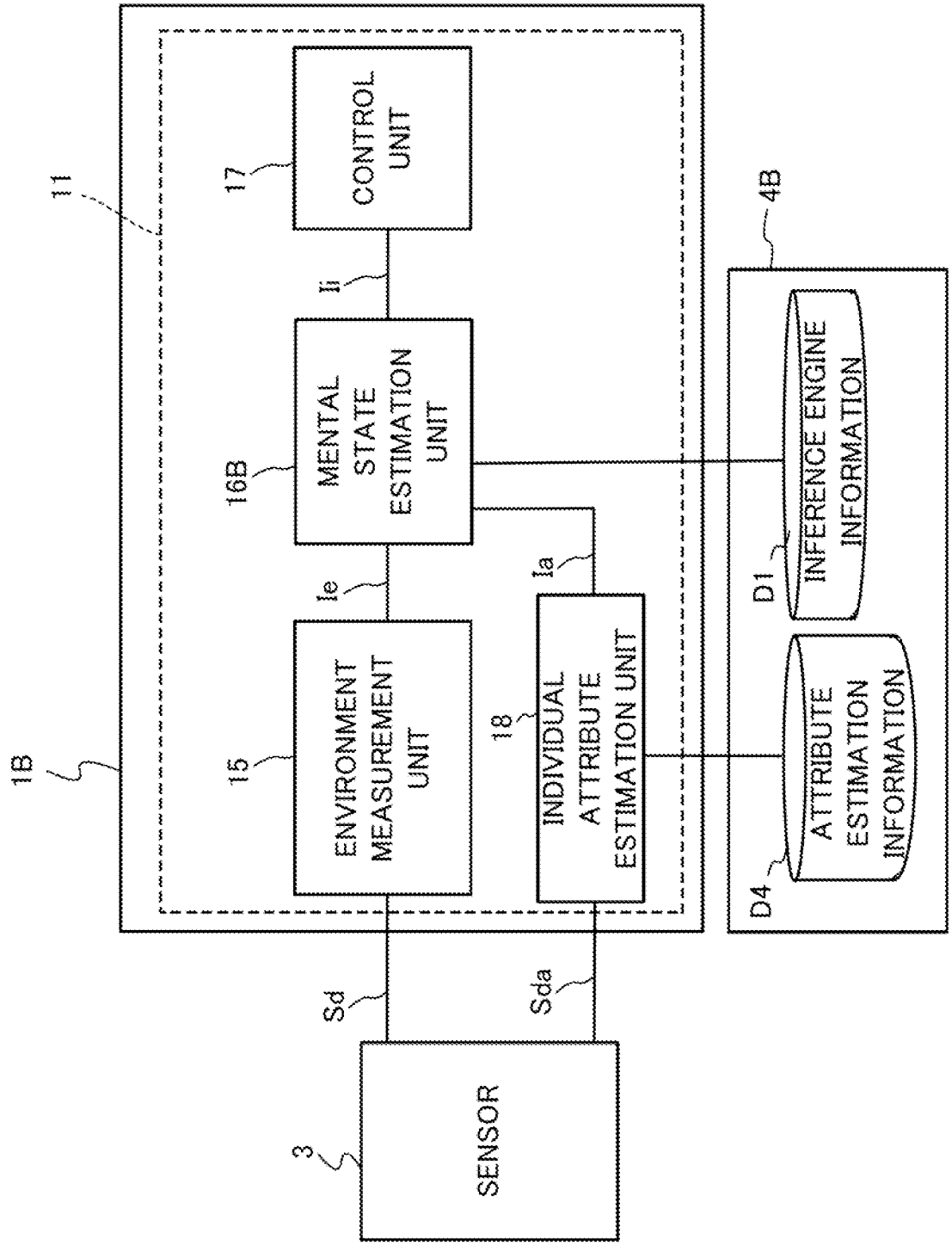
FIG. 10 illustrates a functional block diagram of an information processing device according to a second example embodiment.

FIG. 10 shows a functional block diagram of an information processing device 1B according to the second example embodiment. The information processing device 1B according to the second example embodiment further considers one or more attributes of each person belonging to the group in the target space Stag to estimate the mental state of the group. Hereinafter, the same components as in the first example embodiment are appropriately denoted by the same reference numerals, and description thereof will be omitted as appropriate.

The information processing device 1B has a hardware configuration shown in FIG. 2 similarly to the first example embodiment, and the processor 11 of the information processing device 1B includes the environment measurement unit 15, a mental state estimation unit 16B, the control unit 17, and the individual attribute estimation unit 18. Further, the storage device 4B stores the inference engine information D1 and attribute estimation information D4.

The individual attribute estimation unit 18 estimates one or more attributes (also referred to as "individual attributes") of each person of the group present in the target space Stag based on a sensor signal "Sda" supplied from the sensor 3. Here, the term "individual attributes" herein indicates one or more attributes that affect the estimation on the mental state, and examples thereof include gender, age, hobby, taste, and personality. Further, the sensor signal Sda supplied from the sensor 3 is any information available for estimation on the individual attributes, and it may be a part of the sensor signal Sd obtained by the environmental measurement unit 15 or may be different from the sensor signal Sd. The sensor signal Sda is, for example, an image generated by the camera for capturing the target space Stag. Then, the individual attribute estimation unit 18 estimates the individual attributes in the group in the target space Stag based on the sensor signal Sda by referring to the attribute estimation information D4, and supplies the individual attribute information "Ia" indicating the estimated individual attributes to the mental state estimation unit 16B.

Here, supplementary explanation will be given on the method of estimating individual attributes. For example, when estimating the gender and age of each individual as the individual attributes, the individual attribute estimation unit 18 estimates these individual attributes based on an image generated by the camera that captures the target space Stag. In another example, the individual attribute estimation unit 18 may perform estimation on individual attributes such as hobby, taste, and personality based on an image generated by a camera that captures the target space Stag by using a technique for determining hobby, taste, and personality from the state of the action of a person acquired by the camera. In yet another example, when determining the individual attributes using card information, the individual attribute estimation unit 18 may recognize various individual attributes such as hobby, taste, and personality by reading from the card information a questionnaire result obtained in advance.

The attribute estimation information D4 is the information required to estimate the individual attribute from the sensor signal Sda. For example, the attribute estimation information D4 includes parameters of an inference engine which infers one or more individual attributes of each person in an image when the image is inputted thereto. In this case, for example, the above-described inference engine is a learning model based on machine learning, such as a neural network or a support vector machine, and the parameters of the above-mentioned inference engine generated by learning is included in the attribute estimation information D4. When estimating a plurality of types of individual attributes, the parameters of each inference engine which infers each type of the individual attributes may be included in the attribute estimation information D4.

The mental state estimation unit 16B estimates the mental state of the group in the target space Stag based on the environmental information Ie supplied from the environment measurement unit 15 and the individual attribute information Ia supplied from the individual attribute estimation unit 18, and supplies the mental state information Ii indicating the estimated result to the control unit 17. In this case, the mental state estimation unit 16B estimates the mental state for each sub-group (also referred to as "common attribute group") whose members has one or more common individual attributes among the group in the target space Stag, and generates the mental state information Ii indicating the estimation result of the mental state for each common attribute group. The classification described above may be any classification based on individual attributes, such as classification by gender, classification by age, or classification by any combination thereof.

Here, a description will be given of specific examples of the process executed by the mental state estimation unit 16B. In the first example, the inference engine information D1 includes the parameters of an inference engine learned for each of classes classified based on the individual attribute, and the mental state estimation unit 16B selects an inference engine to be applied for each common attribute group based on the individual attribute information Ia. Then, the mental state estimation unit 16B outputs the mental state information Ii indicating the mental state of the each common attribute group by inputting the environmental information Ie to the selected inference engine. The inference engine described above may be a combination of the first inference engine and the second inference engine described with reference to FIG. 4A, or it may be the third inference engine described with reference to FIG. 4B.

In the second example, the learning device 6 learns such an inference engine that outputs the mental state information Ii when the environmental information Ie and the individual attribute information Ia are inputted thereto, and the inference engine information D1 indicating the parameters of the inference engine is stored in the storage device 4. Then, the mental state estimation unit 16B acquires the mental state information Ii for each common attribute group by inputting the environmental information Ie and the corresponding individual attribute information Ia to the inference engine for the each common attribute group. The inference engine described above may be a combination of the first inference engine and the second inference engine described with reference to FIG. 4A, or it may be the third inference engine described with reference to FIG. 4B.

The control unit 17 performs predetermined control based on the mental state information Ii for each common attribute group supplied from the mental state estimation unit 16B. In this case, for example, based on the mental state information Ii of each common attribute group, the control unit 17 calculates one or more representative values (e.g., the average values, weighted average values, median values, the maximum values, and the minimum values) of one or more indices of the mental state of the entire group in the target space Stag thereby to perform any control described in the first example embodiment based on the representative values.

Figure 11:
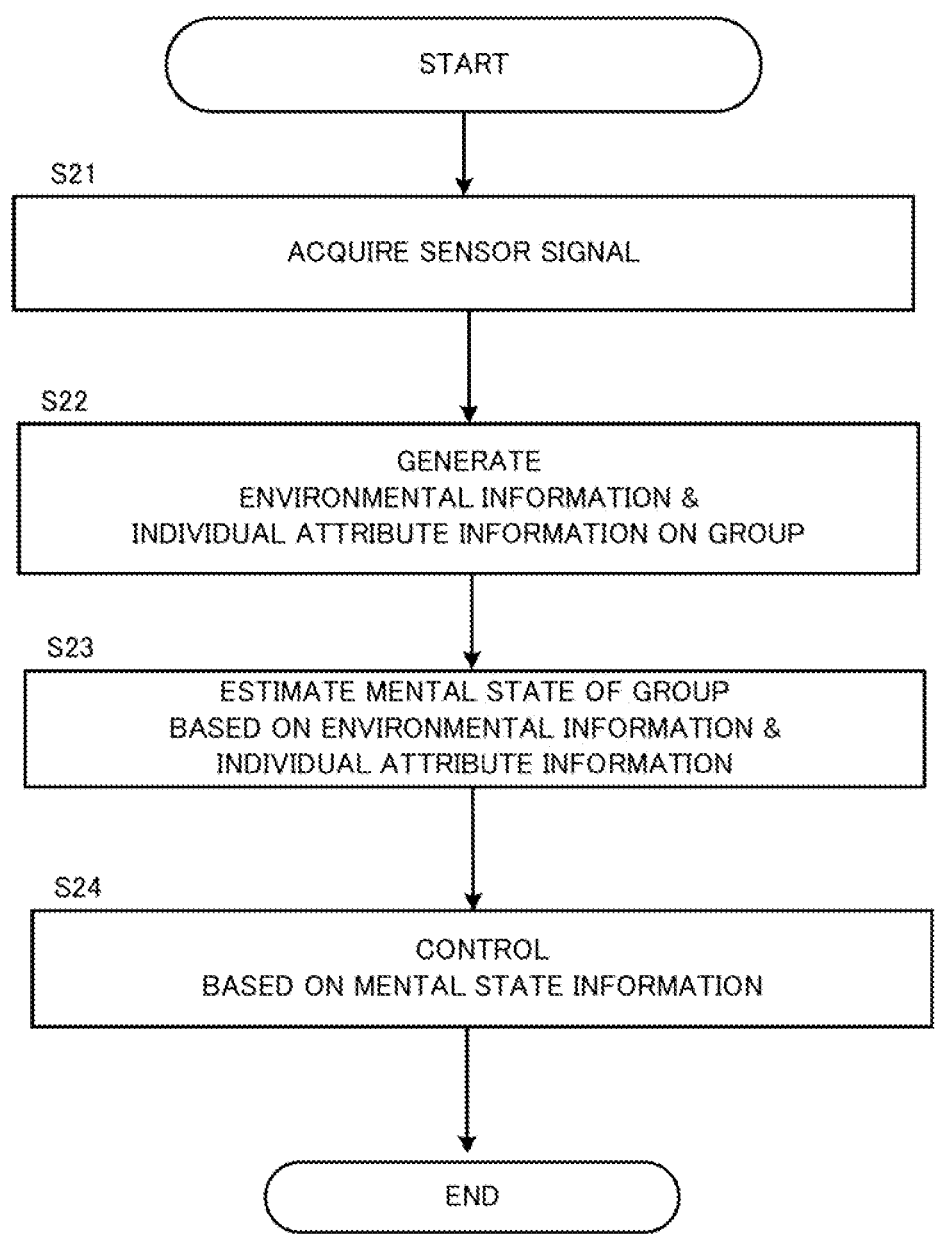
FIG. 11 is an example of a flowchart showing a procedure of the process performed by the information processing device in the second example embodiment.

FIG. 11 is an example of a flow chart illustrating a processing procedure of an information processing device 1B in the second example embodiment. The information processing device 1B may execute the processing of the flowchart shown in FIG. 11 at a timing specified by the user, or may repeatedly execute the processing at predetermined time intervals.

First, the information processing device 1B acquires the sensor signal Sd and the sensor signal Sda generated by the sensor 3 (step S21). In this case, the information processing device 1B receives from the sensor 3 via the interface 13 the sensor signal Stag relating to the environment in the target space Stag and the sensor signal Sd for estimating the individual attributes in the group in the target space Stag. The sensor signal Sda may be part of the sensor signal Sd.

Next, the environment measurement unit 15 of the information processing device 1B generates environmental information Ie based on the sensor signal Sd acquired at step S11. Further, the individual attribute estimation unit 18 of the information processing device 1B refers to the attribute estimation information D4 and generates the individual attribute information Ia on the group in the target space Stag based on the sensor signal Sda (step S22).

Then, the mental state estimation unit 16B refers to the inference engine information D1 and estimates the mental state of the group based on the environmental information Ie and the individual attribute information Ia (step S23). In this case, the mental state estimation unit 16B estimates the mental state for each common attribute group that is a small group having one or more common individual attributes, and generates the mental state information Ii indicating one or more index values of the mental state for each common attribute group. Then, the control unit 17 performs predetermined control based on the mental state information Ii generated by the mental state estimation unit 16B (step S24).

Thus, according to the second example embodiment, the information processing device 1B can further consider the attributes of individuals constituting a group and more accurately estimate the mental state of the group in the target space Stag.

Third Example Embodiment

Figure 12:
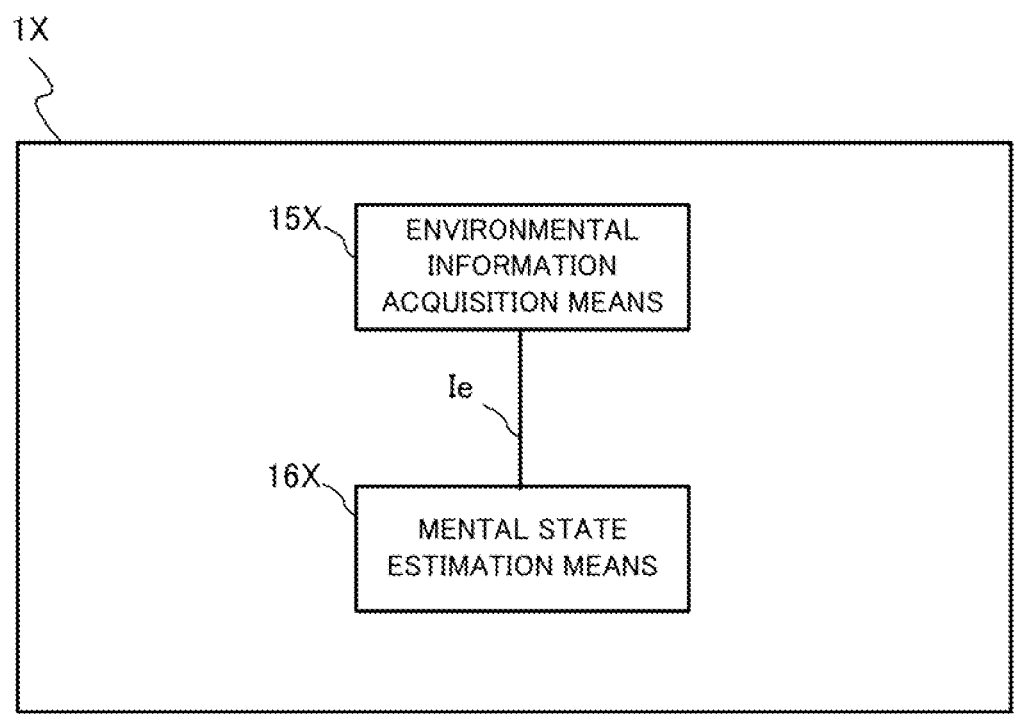
FIG. 12 illustrates a functional block diagram of the information processing device according to a third example embodiment.

FIG. 12 is a functional block diagram of the information processing device 1X according to the third example embodiment. The information processing device 1X mainly includes an environmental information acquisition means 15X and a mental state estimation means 16X.

The environmental information acquisition means 15X is configured to acquire environmental information "Ie" which is information on environment. For example, the environmental information acquisition means 15X may be an environment measurement unit 15 in the first example embodiment (including the above-mentioned modification, it is also true for the following description). In another example, the environmental information acquisition means 15X may receive the environmental information Ie from an external device having a function corresponding to the environment measurement unit 15 in the first example embodiment.

The mental state estimation means 16X is configured to estimate, based on the environmental information Ie, a mental state of a group present in the environment indicated by the environmental information Ie. Examples of the mental state estimation means 16X include the mental state estimation unit 16 in the first example embodiment and the mental state estimation unit 16B in the second example embodiment.

Figure 13:
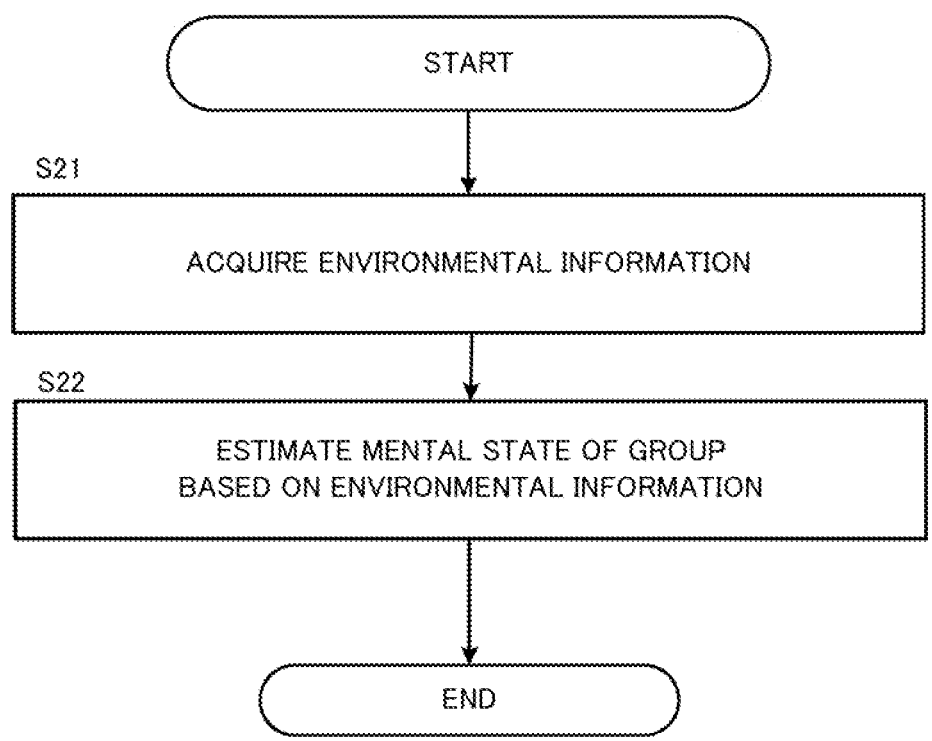
FIG. 13 is an example of a flowchart showing a procedure of the process performed by the information processing device in the third example embodiment.

FIG. 13 is an example of a flowchart executed by the information processing device 1X in the third example embodiment. First, the environmental information acquisition means 15X acquires environmental information Ie which is information on environment (step S21). Then, the mental state estimating means 16X estimates, based on the environmental information Ie, a mental state of a group present in the environment indicated by the environmental information Ie (step S22).

The information processing device 1X according to the third example embodiment can suitably estimate a mental state of a group present in a particular environment.

In the example embodiments described above, the program is stored by any type of a non-transitory computer-readable medium (non-transitory computer readable medium) and can be supplied to a control unit or the like that is a computer. The non-transitory computer-readable medium include any type of a tangible storage medium. Examples of the non-transitory computer readable medium include a magnetic storage medium (e.g., a flexible disk, a magnetic tape, a hard disk drive), a magnetic-optical storage medium (e.g., a magnetic optical disk), CD-ROM (Read Only Memory), CD-R, CD-R/W, a solid-state memory (e.g., a mask ROM, a PROM (Programmable ROM), an EPROM (Erasable PROM), a flash ROM, a RAM (Random Access Memory)). The program may also be provided to the computer by any type of a transitory computer readable medium. Examples of the transitory computer readable medium include an electrical signal, an optical signal, and an electromagnetic wave. The transitory computer readable medium can provide the program to the computer through a wired channel such as wires and optical fibers or a wireless channel.

The whole or a part of the example embodiments (including modifications, the same shall apply hereinafter) described above can be described as, but not limited to, the following Supplementary Notes.

[Supplementary Note 1]

An information processing device comprising:

an environmental information acquisition means configured to acquire environmental information which is information on environment; and a mental state estimation means configured to estimate, based on the environmental information, a mental state of a group present in the environment indicated by the environmental information.

[Supplementary Note 2]

The information processing device according to Supplementary Note 1, wherein the mental state estimation means is configured to estimate biological information feature values, which indicates feature values of biological information on the group, based on the environmental information, and estimates the mental state based on the biological information feature values.

[Supplementary Note 3]

The information processing device according to Supplementary Note 1 or 2, further comprising an individual attribute estimation means configured to estimate an attribute of each individual which belongs to the group, and wherein the mental state estimation means is configured to estimate the mental state based on the environmental information and the attribute of the each individual.

[Supplementary Note 4]

The information processing device according to Supplementary Note 3, wherein the individual attribute estimation means is configured to estimate the attribute of the each individual based on an image generated by a photographing unit which photographs a space in which the group is present.

[Supplementary Note 5]

The information processing device according to any one of Supplementary Notes 1 to 4,
wherein the mental state estimation means is configured to estimate the mental state based on a first inference engine and a second inference engine,
the first inference engine being learned to infer biological information feature values indicating feature values of biological information on the group when the environmental information is inputted thereto,
the second inference engine being learned to infer the mental state when the biological feature information values is inputted thereto.

[Supplementary Note 6]

The information processing device according to any one of Supplementary Notes 1 to 4,
wherein the mental state estimation unit is configured to estimate the mental state based on an inference engine being learned to infer the mental state when the environmental information is inputted thereto.

[Supplementary Note 7]

The information processing device according to Supplementary Note 6,
wherein, when a combination of the environmental information and biological information feature values indicating feature values of biological information on the group are given as training data, the inference engine is leaned by:
using the environmental information as input data; and
using the mental state estimated based on the biological information feature values as correct answer data.

[Supplementary Note 8]

The information processing device according to any one of Supplementary Notes 1 to 7,
wherein the environmental information acquisition unit is configured to acquire, as the environmental information, information relating to:
the number of people belonging to the group;
degree of congestion of the group; or
degree of environmental inferiority of the group.

[Supplementary Note 9]

A control method executed by an information processing device, the control method comprising:
acquiring environmental information which is information on environment; and
estimating, based on the environmental information, a mental state of a group present in the environment indicated by the environmental information.

[Supplementary Note 10]

A storage medium storing a program executed by a computer, the program causing the computer to function as:
an environmental information acquisition means configured to acquire environmental information which is information on environment; and
a mental state estimation means configured to estimate, based on the environmental information, a mental state of a group present in the environment indicated by the environmental information.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. All Patent and Non-Patent Literatures mentioned in this specification are incorporated by reference in its entirety.

DESCRIPTION OF REFERENCE NUMERALS 1, 1A, 1B, 1X Information processing device
3 Sensor
4 Storage device
6 Learning device
D1 Inference engine information
D2 Training data
D3 Accumulated sensor information
D4 Attribute estimation information
100, 100A Mental state estimation system

What is claimed is:

1. An information processing device comprising:
at least one memory configured to store instructions; and
at least one processor configured to execute the instructions to:
acquire environmental information which is information on environment;
estimate an attribute of each individual which belongs to a group present in the environment;
classify the group into sub-groups based on the attribute of each individual;
estimate, based on the environmental information, mental states of the sub-groups; and
estimate a mental state of the group based on the estimated mental states of the sub-groups.

2. The information processing device according to claim 1,
wherein the at least one processor is configured to execute the instructions to estimate biological information feature values, which indicates feature values of biological information on the group, based on the environmental information, and estimates the mental state based on the biological information feature values.

3. The information processing device according to claim 1,
wherein the at least one processor is configured to execute the instructions to estimate the mental state based on the environmental information and the attribute of each individual.

4. The information processing device according to claim 3,
wherein the at least one processor is configured to execute the instructions to estimate the attribute of each individual based on an image generated by a camera which photographs a space in which the group is present.

5. The information processing device according to claim 1,
wherein the at least one processor is configured to execute the instructions to estimate the mental state based on a first inference engine and a second inference engine,
the first inference engine being learned to infer biological information feature values indicating feature values of biological information on the group when the environmental information is inputted thereto,
the second inference engine being learned to infer the mental state when the biological feature information values is inputted thereto.

6. The information processing device according to claim 1,
wherein the at least one processor is configured to execute the instructions to estimate the mental state based on an inference engine being learned to infer the mental state when the environmental information is inputted thereto.

7. The information processing device according to claim 6,
wherein, when a combination of the environmental information and biological information feature values indicating feature values of biological information on the group are given as training data, the inference engine is leaned by:
using the environmental information as input data; and
using the mental state estimated based on the biological information feature values as correct answer data.

8. The information processing device according to claim 1,
wherein the at least one processor is configured to execute the instructions to acquire, as the environmental information, information relating to:
the number of people belonging to the group;
degree of congestion of the group; or
degree of environmental inferiority of the group.

9. A control method executed by an information processing device, the control method comprising:
acquiring environmental information which is information on environment;
estimating an attribute of each individual which belongs to a group present in the environment;
classifying the group into sub-groups based on the attribute of each individual;
estimating, based on the environmental information, mental states of the sub-groups; and
estimating a mental state of the group based on the estimated mental states of the sub-groups.

10. A non-transitory computer readable storage medium storing a program executed by a computer, the program causing the computer to:
acquire environmental information which is information on environment;
estimate an attribute of each individual which belongs to a group present in the environment;
classify the group into sub-groups based on the attribute of each individual;
estimate, based on the environmental information, mental states of the sub-groups; and
estimating a mental state of the group based on the estimated mental states of the sub-groups.

* * * * *